United States Patent [19]

Bentley

[11] Patent Number: 4,978,346
[45] Date of Patent: Dec. 18, 1990

[54] LASER THERMAL PROBE
[75] Inventor: Joseph R. Bentley, Holladay, Utah
[73] Assignee: HGM Medical Laser Systems, Inc., Salt Lake City, Utah
[21] Appl. No.: 392,467
[22] Filed: Aug. 11, 1989
[51] Int. Cl.⁵ .......................... A61B 17/36; A61F 7/00
[52] U.S. Cl. ............................................ 606/27; 606/7; 606/28; 606/31; 128/398; 128/399
[58] Field of Search .................................. 128/395–399, 128/303.1; 606/1, 2, 7, 13–16, 27–31

[56] References Cited
U.S. PATENT DOCUMENTS

| | | | |
|---|---|---|---|
| 4,662,368 | 5/1987 | Hussein et al. | 606/7 X |
| 4,760,845 | 8/1988 | Kovalcheck | 128/398 X |
| 4,773,413 | 9/1988 | Hussein et al. | 128/398 X |
| 4,860,743 | 8/1989 | Abela | 606/7 |
| 4,899,741 | 2/1990 | Bentley et al. | 128/398 X |

Primary Examiner—Robert A. Hafer
Assistant Examiner—Kerry Owens
Attorney, Agent, or Firm—Olive & Olive

[57] ABSTRACT

An improved laser-energizable thermal probe system comprises a thermally conductive probe body having a curvoidal tip and a neck portion for receiving the distal portion of an optical fiber. Each spine of a plurality of spines is attached to the neck portion and extends proximally along the optical fiber for a length substantially longer than the length of the neck portion. Thermally conductive parallel wires are helically wound around the neck and spines and extend along the optical fiber. The wires are interwoven with the spines, and extend in helical coils around the spines to near the end of the spines, where they are crimped into the fiber jacket and thereafter potted with a biocompatible adhesive.

12 Claims, 5 Drawing Sheets

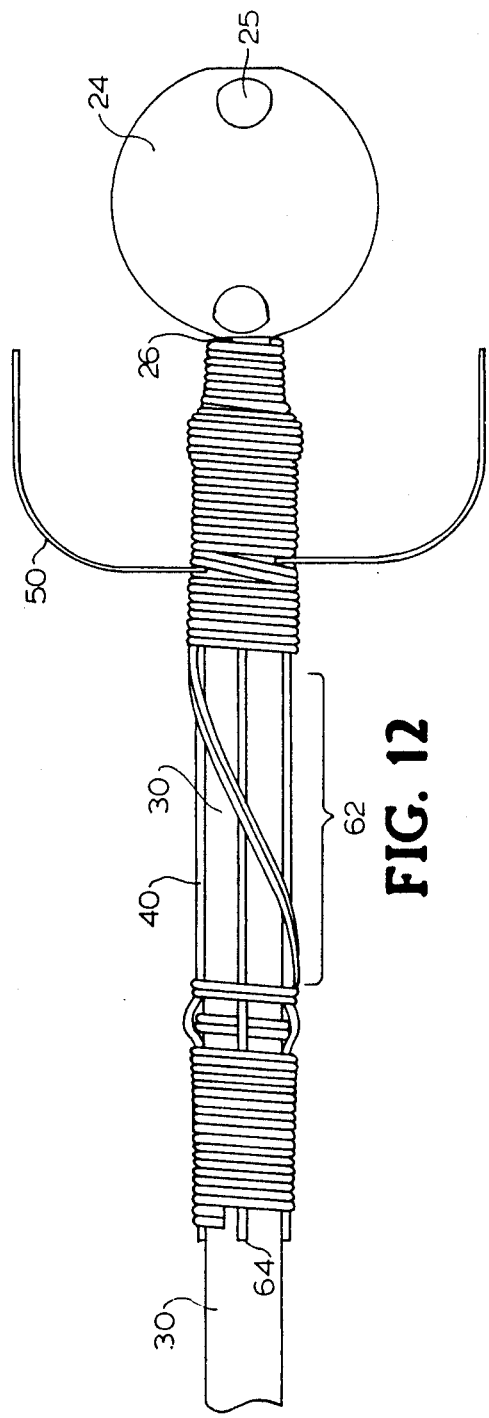
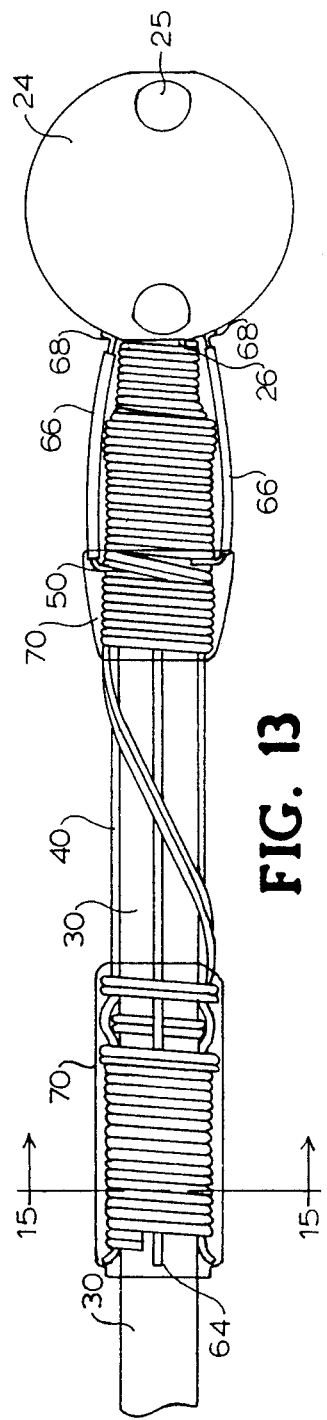

LASER THERMAL PROBE

BACKGROUND OF THE INVENTION

1. Field of the Invention

This invention relates to an improved laser-energized heating probe having a temperature sensor at the distal end of an optical fiber and which is associated with a temperature control. The invention has particular utility in angioplasty procedures wherein tissue is heated for the recanalization of occluded blood vessels by removal of intravascular plaque and thrombi therefrom, as well as in other blood vessel and heating tissue treatments.

2. Description of the Related Art

Art related to the present invention is described in U.S. Pat. No. 4,760,845 and in copending U.S. patent application Ser. Nos. 180,188 (now U.S. Pat. 4,899,740), and 233,478 (now U.S. Pat. No. 4,890,898), which are incorporated by reference herein. Selected references from such art and their pertinent teachings are more fully described below by way of specific background to the present invention.

Aspects of the present invention concern an improved thermally conductive device and temperature sensing system for a laser-energized heating probe and which may be used as a modification of the laser systems described in the aforementioned U.S. Pat. No. 4,760,845 and copending U.S. applications Ser. Nos. 180,188 and 233,478. As discussed in these related patent applications and patent, occlusive heart disease involving blockage of vital coronary arteries is a major cause of death among persons in the adult population. The treatment of patients with occlusive arterial disease generally has been affected by two primary methods: pharmacological treatments for moderate arterial obstructions, and surgical treatments, including arterial bypass surgery and/or percutaneous transluminal angioplasty (PTA), in instances of severe stenosis. Although there are a number of advantages of PTA, a primary disadvantage of this treatment is that the material causing the arterial blockage such as arterial plaque or thrombi is not removed but only pushed aside, with the possibility of future occlusions resulting from the continued accretion of plaque and/or thrombi on the displaced occluding deposits.

Laser irradiation has been proposed for the permanent removal of the aforementioned material deposits. The present invention insofar as it applies to laser angioplasty procedures is basically directed to laser irradiation referred to here as the indirect laser irradiation technique and involves the insertion of an optical fiber into the arterial or venous channel to function as a transmissive element for delivery of laser energy to a thermally conductive device disposed at the treatment site. Cooling and temperature control of the probe are of critical importance and constitute primary concerns in the use of such laser-energized devices.

Another primary concern in the use of the aforementioned probe devices is ensuring that the thermally conductive structure is suitably attached to the optical fiber such that it will not become disengaged during use. Federal Republic of Germany Patent No. 2,826,383 published Dec. 20, 1979 as well as two later U.S. patents (U.S. Pat. No. 4,646,737 and U.S. Pat. No. 4,662,368) disclose a heat generating element comprising a metal probe body mounted on an optical fiber through which laser energy is transmitted to the probe body to generate heat energy. The German patent discloses cooling of the probe device by flowing a gas or a fluid to extract heat from the heat generating element. While these patents refer to sensing the temperature and in some cases by use of a thermocouple attached to the heat generating element, none of the referred to patents disclose means for both sensing and controlling the temperature of the heat generating element.

The two U.S. patents mentioned in the preceding paragraph do however disclose monitoring probe temperature by monitoring reflected infrared radiation emanating from the laser-energized heated probe after the laser energy source is deactivated. Such a method does not lend itself to real time monitoring or control of probe temperature since the laser is in fact turned off while measurements are made during the cooling cycle of the probe. These probes rely heavily on a dosimetry matrix to estimate probe temperature, with prior in-vitro data having been accumulated in the matrix relating probe temperature to input laser power level. Such a dosimetry matrix is highly variable and dependent upon the fluid dynamic environment surrounding the probe body, resulting in potentially large deviations from predicted probe temperatures. See also an article by George S. Abela et al entitled "Hot Tip: Another Method of Laser Vascular Recanalization" published in *Surgery and Medicine* 5:327–335, 1985.

The laser energized thermal probe described in commonly-owned U.S. Pat. No. 4,760,845 employs a coiled wire as a means of joining the probe body to the optical fibers and preventing the probe from becoming disengaged during use. This helically wound wire also serves as a means for dissipating heat generated by the probe in use, thereby preventing the heat thus generated from reaching the area where the tip is mechanically attached to the optical fiber jacket and avoiding the need for cooling fluids and the like. A mass of a laser energy-absorptive, thermally conductive, high emissivity medium is contained within the interior of the probe tip to maximize the absorption of the laser energy by the probe.

Prior copending U.S. application Ser. No. 180,188 discloses a thermal probe assembly which comprises means for real time sensing and controlling of the temperature of the heat generating element, and responsively controlling the laser power to maintain some predetermined temperature. Temperature sensing and monitoring has also been accomplished with an element separate from the optical fiber, as described in U.S. Pat. No. 4,476,512.

In electrically heated vascular probes, which typically comprises a large hollow cylinder and an inner heater coil, a thermocouple element may be contained within the heater coil inside the probe tip. Such electrical probes are however characterized by slow response times and limited temperature responsiveness, and inherently require the presence of electrical current at the probe tip site. See the article, "The Heated Probe: A New Endoscopic Method For Stopping Massive Gastrointestinal Bleeding" by Robert L. Protell et al., *Gastroenterology* 74, pages 257–262 (1978).

Accordingly, it is an object of the present invention to provide a laser-energizable heat probe assembly capable of operating at relatively high temperatures, which does not require the introduction of an externally supplied coolant medium to the treatment site, and possesses a high degree of structural integrity.

A further object of this invention is to provide a thermocouple-equipped laser energizable heated probe assembly in which temperatures are readily monitored via a temperature sensing thermocouple associated with the laser heated probe and coupled to a laser power control system.

A further and significant object of the invention is to provide a probe assembly having improved means for securely attaching the probe body to the optical fiber.

Other objects and advantages will be more fully apparent from the ensuing disclosure and appended claims.

SUMMARY OF THE INVENTION

The present invention relates to a laser-energizable thermal probe assembly of the type in which a probe body is connected to a distal end of an optical fiber and the optical fiber is coupleable at a proximal end to a laser energy source. The laser energy is converted to thermal energy which heats the probe body through the interaction of the laser beam with a laser-energy, absorptive, thermally conductive, high emissivity medium operatively associated with the probe body. As used herein, "proximal" and "distal" refer to portions of the assembly toward and away from the laser source, respectively. The thermal probe assembly comprises:

(a) a thermally conductive probe body having a curvoidal tip and a neck portion joined to said tip and extending proximally therefrom, with an interior passage in said probe body extending through said neck portion and receiving the distal end of an optical fiber so that laser energy from a laser energy source coupled to the proximal end of the optical fiber is transmitted by the optical fiber to the probe body and converted to thermal energy transmitted by the tip to a selected site in contact with the tip;

(b) a plurality of spines parallelly aligned with each other and with the optical fiber, each spine having a distal spine end, a central spine area and a proximal spine area, with said distal spine ends being attached to the neck portion of the probe body and said spines extending proximally therefrom for a length substantially longer than the length of said neck portion and along and adjacent a distal portion of the length of the optical fiber; and (c) a plurality of wires, parallelly wound in a series of helical turns around the probe body neck portion, and around the distal end, central and proximal spine areas of said spines and around said optical fiber distal portion, with said helical turns extending from the probe body neck portion to the proximal spine areas and with said wires being secured to the spines and with said central and proximal spine areas being effectively secured to said optical fiber by crimping of said wires.

More particularly, the invention comprises a thermal probe assembly with, for example, four to ten spines equally circumferentially spaced-apart about the circumference of the optical fiber. Preferably, the spines are formed of an annealed platinum/iridium alloy and the thermally conductive wires are formed of a metal selected from the group consisting of platinum, iridium, and alloys thereof.

In the preferred embodiment of the invention, the series of helical turns comprises:

(a) a plurality of contiguous helical turns extending from the probe body neck portion to the central spine areas;

(b) at least one non-contiguous helical turn extending from the contiguous helical turns to the proximal spine areas;

(c) a plurality of proximal helical turns interwoven with the spines in said proximal spine areas; and (d) a plurality of contiguous helical turns continuing to the proximal end of said spines.

The helical turns are crimped and then potted with a cured mass of biocompatible adhesive extending from the contiguous helical turns over the neck portion to the proximal helical turns.

The thermal probe assembly may include a thermocouple secured proximate and in operative thermal relationship to said probe body to sense the temperature of said probe body, and a pair of thermocouple leads extending from said thermocouple. The thermal probe assembly may further include a jacket surrounding the optical fiber, wherein said thermocouple leads are encased with insulating material and protrude externally from the jacket between adjacent helical turns, with the ends of said thermocouple leads being attached to an exterior surface of the curvoidal tip. The series of helical turns of the thermal probe assembly which includes the thermocouple leads may comprise the contiguous and non-contiguous helical turns discussed above.

BRIEF DESCRIPTION OF THE DRAWINGS

FIG. 12 is a side elevation view of the extended wire wrap and woven spine ends of the probe assembly partially shown in FIG. 11.

FIG. 13 is a side elevation view of the probe assembly of FIG. 12, showing the final positioning of the thermocouple leads, and potting of the wire wrap with a cured mass of a potting composition.

DETAILED DESCRIPTION OF THE INVENTION, AND PREFERRED EMBODIMENTS THEREOF

In angioplasty applications, separation of the probe body from the optical fiber generally necessitates immediate surgical intervention to avoid potentially catastrophic occurrences. This invention provides a probe assembly that will withstand significant tensile and compressive stresses and comprises a very high integrity joining means for connecting the probe body to the optical fiber.

Another primary objective is to provide a means to dissipate heat from the heated probe and to avoid heating areas of the probe assembly not required for treatment. Overheating the non-tip portions of the probe assembly jeopardizes its integrity by subjecting the connecting portions and joints to excessive heat.

In the broadest sense, the preferred thermal probe assembly comprises a probe body, a plurality of spines and thermally conductive wires. Specifically, the probe body comprises a curvoidal tip and a neck portion extending proximally from the curvoidal tip with a high emissivity material placed in an interior passage of the tip. After a ribbon of platinum/iridium material is welded to the neck, the polished end of an optical fiber is inserted into the interior passage. Preferably there are thermocouple leads embedded in an optical fiber jacket material, said leads being attached to form a thermocouple proximate the curvoidal tip. The distal ends of a plurality of spines are welded to the platinum-iridium ribbon which has been welded to the neck. The distal ends of dual wires are welded to the neck distal to said ribbon. These wires reside side by side and are wound in parallel towards the proximal end of the optical fiber and welded to the spines. The distal ends of the thermocouple leads are preferably extended outward between adjacent turns of the wires and then toward the tip. One or more loose turns of the wires are located proximal from the other side by side turns. At a distance from the proximal end of the spines, a plurality of turns of the wires is interwoven with the spines, and a plurality of contiguous helical turns continue to the end of the spines. The turns of the wires, except for those nearest the neck are overlaid with a biocompatible adhesive substance.

Figure 1:
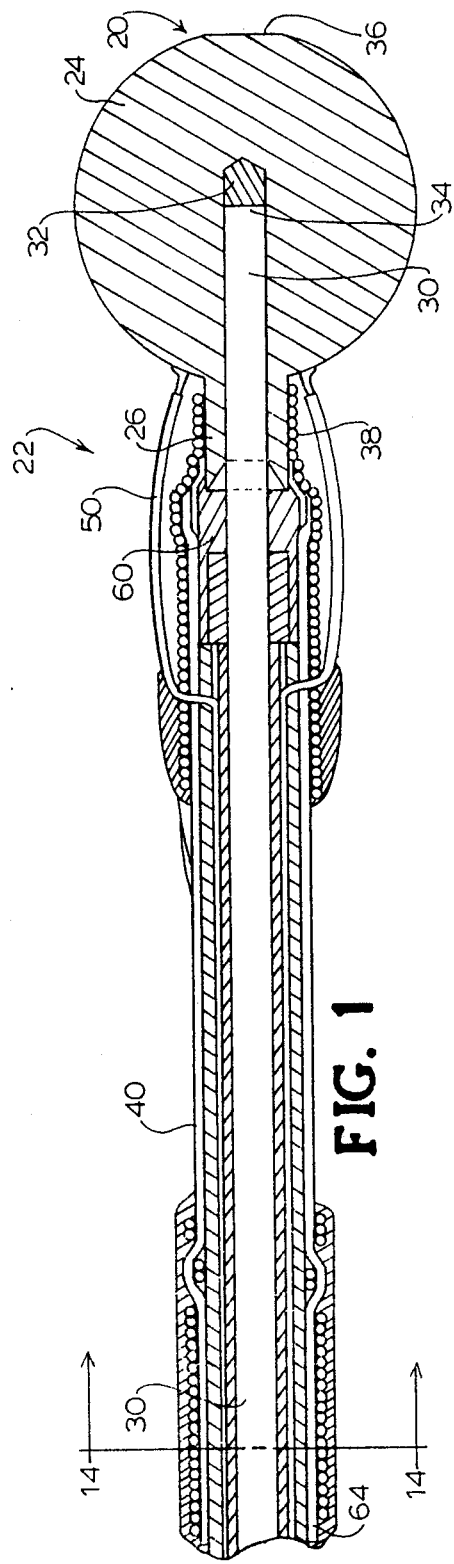
FIG. 1 is a sectional side elevation view of a probe assembly according to a first embodiment of the present invention.
Figure 2:
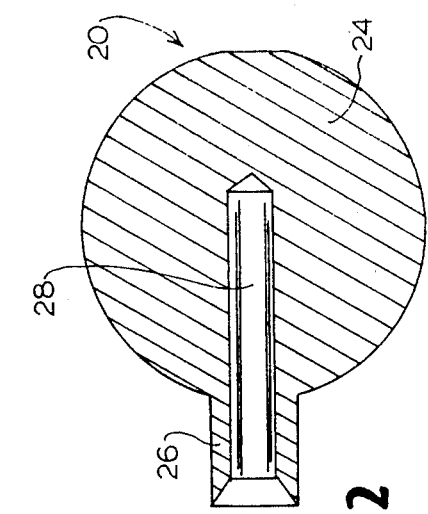
FIG. 2 is a sectional side elevation view of the probe body of the FIG. 1 probe assembly.

Referring to the drawings, for purposes of the present invention probe body 20 of the probe assembly 22 is formed as described in U.S. Pat. No. 4,760,845 of a suitable heat-conductive material, preferably a metal (FIGS. 1 and 2). Suitable illustrative metal materials include platinum, iridium, platinum/iridium alloys and various stainless steels and their alloys. Platinum/iridium alloys are the preferred materials of construction. The probe body 20 (FIG. 1) comprises a curvoidal probe tip 24 and cylindrical probe neck 26. The curvoidal probe tip 24 may be of a shape selected from the group consisting of spherical, spheroidal and ellipsoidal shapes, with spherical shapes being preferred as discussed in U.S. Pat. No. 4,760,845. Other embodiments of the tip of this invention may be those discussed in co-pending application Ser. No. 180,188 thus, the tip may be substantially spherical with small localized planar distal face and include an interior guide passage 25 as disclosed therein and also shown in FIGS. 8–9 and 11–13. The tip alternatively may have an exterior concave recess 27 to accommodate a guide wire as in FIG. 5.

It will be appreciated that the dimensions of the various embodiments illustratively set forth herein are for the purpose of facilitating understanding of the invention, and that other dimensions and dimensional relationships may be employed within the broad scope of the invention. In general, the cross-sectional diameter of the probe body's tip may range from about 1 to about 4 millimeters.

Tips having a diameter of only 1.5 to 2.0 mm do not generally require the use of a guide wire because the probe itself is highly guidable. Larger probes may usefully have guide wires employed therewith and be used with the thermocouple. The diameter of the neck may be about 0.58 to 0.62 mm with the neck length being about 0.8 mm.

The probe body 20 may be integrally formed by any suitable method such as casting, molding, machining, etc. Although the probe body 20 may be comprised of separately formed tip and probe elements, it is generally preferred to provide the probe body 20 as an integrally formed article to ensure its structural integrity under the stress conditions encountered in use of the invention.

As shown in FIG. 2, the probe body 20 has a central interior passage 28 extending through the neck 26 into the spherical probe tip 24. The interior diameter of this passage is made large enough to accept the fiber size which is to be utilized, and is made somewhat larger if the thermocouple leads are in the interior passage (see below). The central interior passage 28 is preferably coaxial with the central axis of the probe body 20 so that the optical fiber 30 (FIG. 1) which is inserted into the central interior passage 28 is centrally accommodated and uniform radial heat transfer is effected.

While the distal end 34 of optical fiber 30 may make direct contact with the distal end surface of passage 28, it is desirable that high emissivity material 32 be placed in the interior passage 28 of tip 24 (FIG. 1). The term "high emissivity" as used herein means an emissivity of at least 0.80 and preferably is taken as 1.0. A preferred material for the high emissivity material 32 is nuclear grade compressed graphite. Other suitable high emissivity, high absorptivity, low reflectance materials that are responsive to laser energy to convert it into thermal energy for transmission to the tip may be employed, for example, carbon black, platinum oxide powder, etc. The high emissivity material 32 is preferably placed centrally in the tip 24 so that it abuts the polished face of the distal light-emitting end 34 of optical fiber 30. Laser energy transmitted by the optical fiber 30 impinges on the high emissivity material 32 and is converted to thermal energy which is then transmitted via conduction and radiation to the tip 24. Tissue or other material placed in contact with the external surface 36 of tip 24 is consequently subjected to rapid, intense heating.

Figure 3:
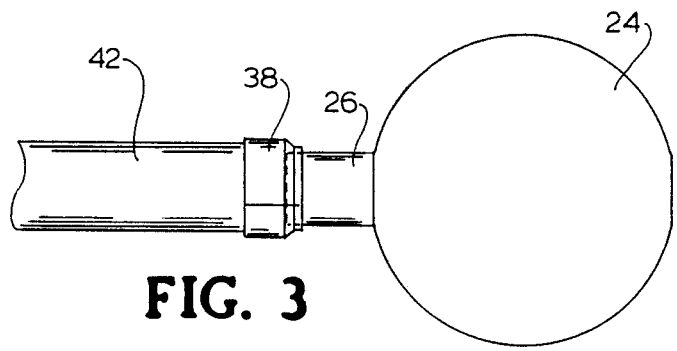
FIG. 3 is a side elevation view of a portion of the probe assembly of FIG. 1.

As in pending patent application Ser. No. 180,188, a platinum/iridium ribbon 38 is welded on to neck 26 (FIG. 3) to extend beyond the end of the neck by about 0.3 mm. For this step and the subsequent welding to spines 40 as discussed below, a mandrel 42 is used to appropriately position the ribbon 38, spines 40 and later wound thermally conductive platinum/iridium wires 44A, 44B.

Figure 4:
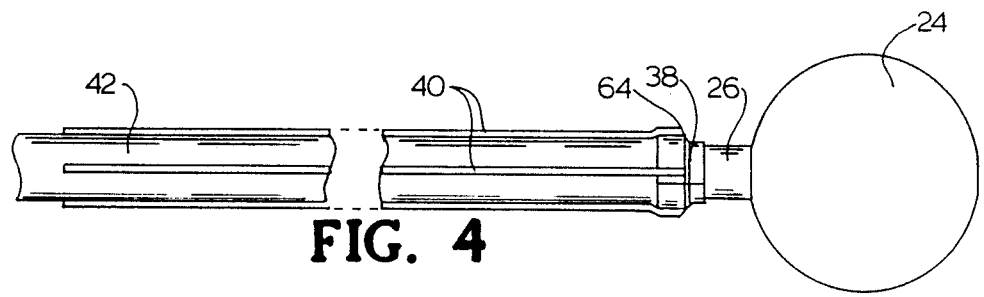
FIG. 4 is a side elevation view of a portion of the FIG. 1 probe assembly showing spines welded to a collar joining the probe body and optical fiber.
Figure 5:
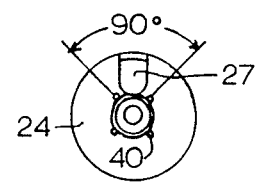
FIG. 5 is an end elevation view of a second embodiment of the probe body and collar with the optical fiber omitted for clarity, to show the spine locations.
Figure 6:
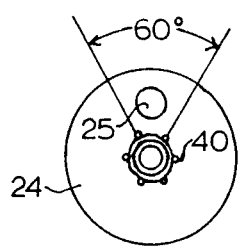
FIG. 6 is an end elevation view of the first embodiment of the probe assembly.
Figure 7:
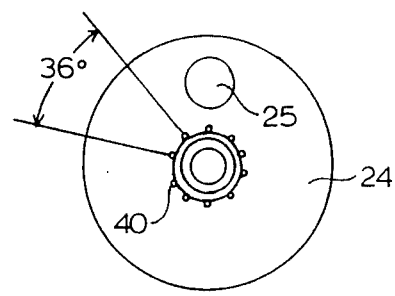
FIG. 7 is an end elevation view of the spine locations in a third embodiment of a probe assembly.

Whereas the probe assembly of the prior co-pending application Ser. No. 180,188 utilized relatively short spines primarily to facilitate welding adjacent wire coils, the probe assembly of the present application teaches lengthened spines 40 welded to the neck 26 and extending proximally. As shown in FIG. 4, a plurality of circumferentially spaced spines 40 (preferably four to ten) is attached to the platinum/iridium ribbon 38 with the distal end of each spine 40 being welded to the platinum/iridium ribbon 38 at equally spaced positions. The spines 40, of about 0.003 inches in diameter, extend parallel to each other proximally for a distance substantially longer than the length of the neck 26. The preferable number of spines 40 will depend directly on the size of optical fiber being used. The cross-sectional angle between the position of the spines decreases with an increased number of spines 40. Thus, for small size tips four spines 40 are used as shown in FIG. 5 and an angle of 90 degrees is formed between the circumferential positions of the spines 40. In another example, when an intermediate size tip is used, six spines 40 are employed as in FIG. 6 and a 60 degree angle is formed between the spines and in a further example for a large size tip ten spines 40 are separated by a 36 degree angle as in FIG. 7.

Long annealed wires 44A, 44B are dually wrapped about the platinum/iridium ribbon on the neck 26 and in the spine area in two phases, the phases being separated sequentially from each other by the process of attachment of the optical fiber assembly 46 to the probe assembly 22. The preferred material for the wires is a platinum/iridium alloy, but a different thermally conductive material may be used. A typical wire would have a cross sectional diameter of 0.076 mm.

Figure 8:
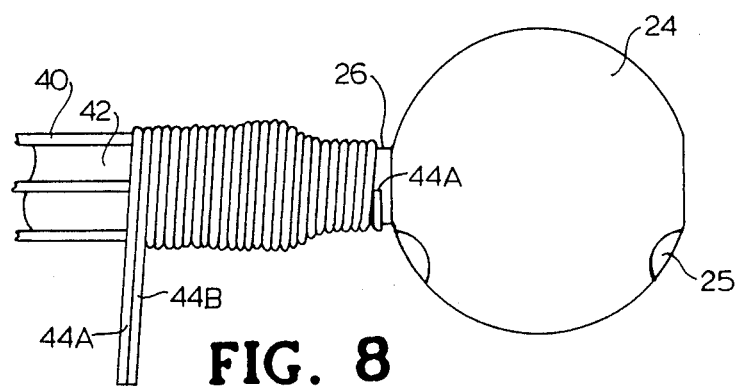
FIG. 8 is a side elevation view of a first side of a probe assembly according to the first embodiment of the invention, showing how the wrapping of a first wire is initiated.
Figure 9:
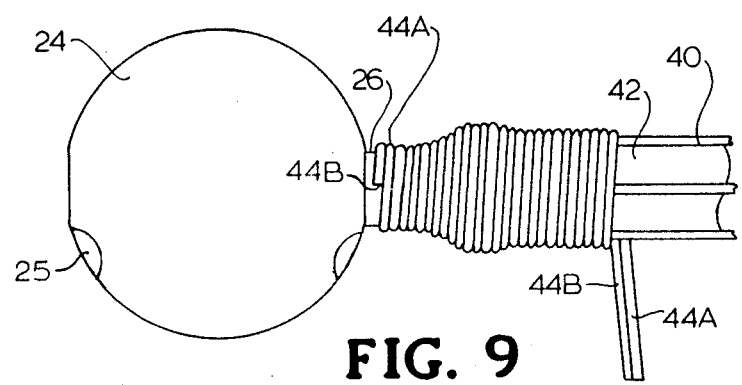
FIG. 9 is a side elevation view of a second side of the FIG. 8 probe assembly, showing how the wrapping of a second wire is initiated.

The first phase of dual wire wrapping begins by welding the end of a first annealed wire 44A tangentially to the probe neck 26 next to the spherical probe tip 24 (FIG. 8). The first wire 44A is wrapped 180° around the neck 26 and the end of a second annealed wire 44B is welded to the neck next to the first wire 44A (FIG. 9). Both wires 44A, 44B are welded again after one full wrap of the first wire and one-half wrap of the second wire. As the wrapping continues, the wires 44A, 44B are not overlapped on to each other but continue contiguously without overlapping. The frequency of wire welds to the underlying spines must be sufficient for secure attachment. The welds are preferably located every 90°, 60°, or 36° depending on the size tip for the first 1½ wraps with both wires. On subsequent wraps, welding can be aligned with the spines 40 at every other or each position of each wire. While successive welding of the turns of wire does reduce the effective thermal conduction path provided by the coiled wire, the heat dissipation benefits of the welded wire coils are still greater than that of a tubular heat dissipation structure. Welding of adjacent coils to the spines is preferred because it allows for finite spacing between the weld points. Such finite spacing between the weld points allows relief of pressure that may be due to heating or other causes. Although welding is preferred, other rigid bonding means may be used to join the coiled wire to the spines. Wrapping of the dual wrap continues proximally down the spines for approximately 10–18 wraps. After appropriate cleaning of the wound and welded wires, the mandrel 42 is carefully withdrawn.

As described in more detail in the related applications, an illustrative dressed optical fiber 30 which has been found useful in the practice of the present invention comprises (i) a 200 micron diameter high-purity quartz optical fiber core, (ii) a 240 micron diameter doped quartz clad layer providing a numerical aperture of 0.24 thereon and (iii) a 260 micron diameter buffer layer formed of HardClad non-optical polymer, manufactured by Ensign-Bickford Industries, Inc., Simsbury, Conn. These layers are covered with the thin jacket 52 (FIG. 10) comprising, in one example, clear Tefzel 210 material manufactured by E.I. duPont de Nemours & Co., Inc., Wilmington, Del. and which serves to separate the thermocouple leads 50 from the lower layers. A 550 micron outer jacket formed of Tefzel 210 material, manufactured by E. I. duPont de Nemours & Co., Wilmington, Del. serves as the final casing. In this construction, the high density plastic buffer layer (iii) serves as a support medium uniformly contacting the doped quartz clad layer (ii) and permitting bending of the fiber, while the outer jacket protects the buffer layer and enhances the flexibility of the fiber. The thin layer of jacket material 52, serves to dissipate the transfer of stresses between the thermocouple leads and the optical fiber core and inner layers which might develop during fabrication of the optical fiber cable or during bending or axial stressing of the optical fiber cable. The jacket 52 comprises a black fluroplastic material useful in preventing the escape of nuisance laser light. Of course, many other sizes, types and configurations of optical fibers may be used in the broad practice of the present invention without departing from the scope and substance thereof.

Figure 10:
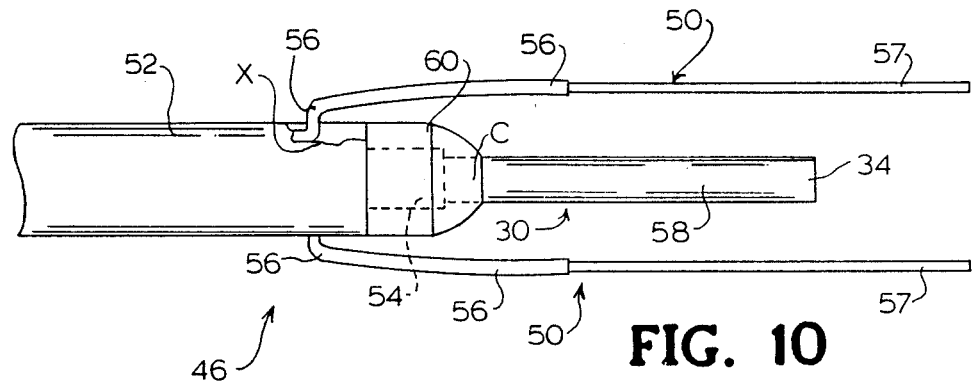
FIG. 10 is a side elevation view of the end portion of an optical fiber and associated thermocouple leads, which may be present in the first, second or third embodiment, prior to securement of a probe body to the optical fiber to form a probe assembly.

The end of the optical fiber is prepared prior to its insertion into the probe tip in the following manner. A suitable length of the distal free end of an optical fiber/plug assembly 46 having two thermocouple wires 50 (as described in the above-cited co-pending applications) is released from the coil of the optical fiber (not shown). A sharp implement such as a razor blade is used to strip away a length of the jacket 52 on the distal end of the optical fiber 30 (FIG. 10). Care is taken not to damage the thermocouple wires 50 each of which has a coating of insulation. These wires are positioned parallel to each other outside the buffer and encased within the jacket as discussed in the co-pending applications. The insulation is preferably a thermally resistant material, for example a Teflon derivative.

In the preferred embodiment, the jacket housing the optical fiber is fabricated to contain the leads from the thermocouple. The leads may be parallel to the optical fiber or may be coiled within the jacket around the optical fiber. The leads are in turn coupled to the temperature control circuitry to which they are electrically connected and function in conjunction with the laser light source and its control as disclosed in the co-pending applications.

The thermally conductive wires and spines of the present invention may be employed with probe assemblies not having thermocouples or with thermocouple arrangements other than that shown. For example, a thermocouple may be positioned internally within the interior passage of the curvoidal tip as disclosed in co-pending application, Serial No. 180,188 with the thermocouple leads adjacent the optical fiber and within the turns of the wires.

The second clear jacket material and hard buffer 54 beneath the jacket 52 is stripped from the distal polished end 34 of the optical fiber 30 to within about 0.5 mm of the new end of the jacket 52. The thermocouple leads 50 are carefully teased back at X for about another 0.4 mm as shown in FIG. 10. The insulation 56 is stripped off the distal end 57 of the thermocouple leads 50 for about half the length of the exposed quartz fiber 58 (slightly more than half the length of the exposed thermocouple lead 50).

A quantity of boron nitride 60 is placed around the optical fiber 30 over the exposed clear jacket and hard buffer 54 at the distal end of the jacket 52 and covers the bare quartz fiber end 58 (FIG. 10 at C). Boron nitride or another appropriate ceramic adhesive with similar characteristics is the preferred substance for filling spaces within the probe assembly because it is a temperature resistant, chemically stable, thermally conductive, thermally shock resistant, electrically insulating compound that helps eliminate pressure build up and gas accumulation within the probe. The filler selected should be in a fluid state when applied.

The stripped end 58 of the optical fiber 30 is inserted with a slight turning motion into the probe assembly 22 after the graphite has been added so that about 0.3 mm of the fiber outer jacket 52 is within the welded area, i.e. within the last 3 or 4 wraps of wire placed in the first phase discussed above. The thermocouple leads 50 at this point protrude from opposite sides 61 of the optical fiber 30 adjacent to the edge of the last wrapped wire. Generally the thermocouple leads 50 should protrude rotated 90° with respect to the tip guide channel on the tip probe as best seen in FIG. 13.

Figure 14:
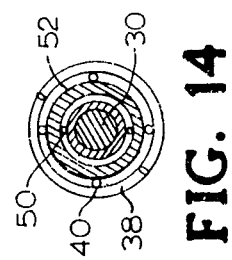
FIG. 14 is a cross section view taken in the direction of line 14–14 of FIG. 1 prior to potting of the wire wrap and prior to crimping of the wire wrap.
Figure 15:
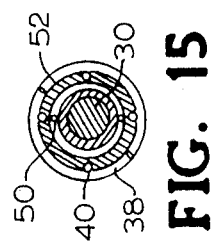
FIG. 15 is a cross section view taken in the direction of line 14–14 of FIG. 1 prior to potting but after crimping of the wire wrap.
Figure 11:
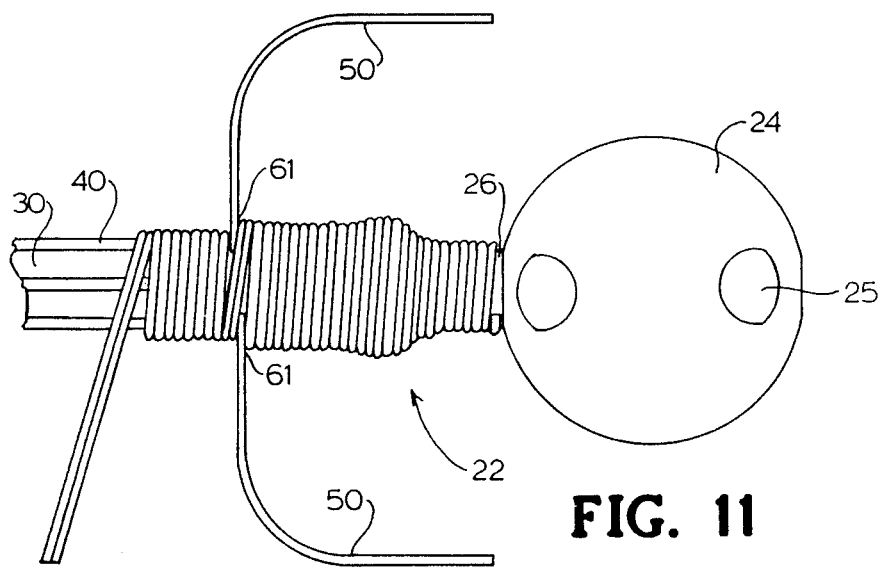
FIG. 11 is a side elevation view of the optical fiber and the thermocouple wires of FIG. 10 being mated with and wrappingly secured to a probe body to form a probe assembly according to the third embodiment.

In the second phase of dual wire wrapping, the contiguous wrapping of the proximal ends of the dual wire wrap is continued around the central spine areas and proximal to the protruding thermocouple leads 50 around the jacket 52 for another 4 to 6 wraps per wire 44A, 44B in the same manner as for the first phase (FIG. 11). One to two non-contiguous helical wraps 62 of the dual wrap are then made toward the proximal end 64 of the spines (FIG. 12). The remaining dual wrapping comprises a plurality of helical turns weavingly wrapped with the spines 40 as shown in FIG. 12. A plurality of helical turns continues to the proximal end 64 of said spines. The helical turns are then crimped. FIG. 14 represents a cross section view taken prior to crimping and FIG. 15 a cross section view taken after crimping. The crimping effectively displaces some of the jacket material 52 and forces such material radially outwardly in the spaces between the wraps. The proximal and central areas of the spines are thus effectively secured to the optical fiber 30.

After the dual wrapping is complete, a length of polyimide tubing 66 is placed over each thermocouple lead 50 by feeding the lead 50 through the tubing 66. Each thermocouple lead 50 is then placed tightly against the welded wraps parallel to the probe neck 26 and the distal end 68 of each thermocouple lead 50 is welded to the proximal surface of the tip probe (FIG. 13) about 180° apart from each other on the probe tip 24 which establishes a desired temperature sensing thermocouple through the tip.

Biocompatible epoxy 70 is applied under heated air to all of the dual wrapped area except the distal wraps (about the first eight wraps) that are welded on to the ribbon and spines, also taking care not to get epoxy and the wraps and spines to the optical fiber jacket 70 on the tip of the probe or on the distal wraps (FIG. 13). The epoxy further bonds the wraps to the spines and provides a smooth outer surface. A biocompatible epoxy coating also preferably covers the exposed surfaces of the thermocouple wires 50 where they protrude from the jacket 52 and enter the polyimide tubing 66. Preferred materials for angioplasty applications include biocompatible epoxies satisfying the criteria for PHS Class 6 materials, such as EE0079/HD0070 epoxy, commercially available from Hysol Division of the Dexter Corporation, Pittsburg, Calif. and EPO-TEK Type 301 epoxy, commercially available from Epoxy Technology, Inc., Billerica, Mass. After curing of the epoxy 70, the entire assembly is inspected and tested for tensile strength. The spines thus bonded to the helical wraps will break in tension prior to pulling out.

While various examples have been given, it may also be mentioned that four spines have been found adequate for securing 200 micron size optical fiber, six spines for securing a 300 micron size optical fiber and ten spines for securing a 600 micron size optical fiber. 200 micron size optical fibers have been employed with 1, 1.5 and 2 millimeter size tips, 300 micron size optical fibers with 2.5 and 3.0 millimeter size tips and 600 micron size optical fibers with 2.5, 3.0, 3.5 and 4.0 millimeter size tips modified as required to accept the fiber and a guide wire when applicable.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A laser-energizable thermal probe assembly for medical treatment comprising:
    (a) an optical fiber extending between distal and proximal ends and having a fiber jacket formed thereon;
    (b) a thermally conductive probe body having a curvoidal tip, a neck portion joined to said tip and extending proximally therefrom and an interior passage in said probe body extending through said neck portion, the distal end of said optical fiber being mounted in said passage enabling laser energy from a laser energy source coupled to the proximal end of the optical fiber to be transmitted by the optical fiber to the probe body and converted to thermal energy to be transmitted by the tip to a selected treatment site in contact with the tip;
    (c) a plurality of spines positioned parallel with each other and with the optical fiber and spaced apart around the optical fiber, each spine having a distal end, a central spine area and a proximal spine area, said distal spine ends being attached to the neck portion of the probe body and said spines extending proximally therefrom for a length substantially longer than the length of said neck portion and along and adjacent a distal portion of the optical fiber;
    (d) a plurality of thermally conductive parallel wires wound in a series of helical turns around the probe body neck portion and around the distal end, central and proximal spine areas of said spines and around said optical fiber distal portion, said helical turns extending from the probe body neck portion to the proximal spine areas and being secured at selected locations to the spines; and (e) securing means operative to secure the spines, wires and optical fiber together.

2. A laser-energizable thermal probe assembly according to claim 1 in which said plurality of spines comprise three to ten spines equally circumferentially spaced-apart about the circumference of the optical fiber.

3. A laser-energizable thermal probe assembly according to claim 1, wherein said thermally conductive wires are formed of a metal selected from the group consisting of platinum, iridium, and alloys thereof.

4. A laser-energizable thermal probe assembly according to claim 1, wherein the series of helical turns comprises:
 (a) a plurality of contiguous helical turns extending from the probe body neck portion to the central spine areas;
 (b) at least one non-contiguous helical turn extending from the contiguous helical turns to the proximal spines area;
 (c) a plurality of proximal helical turns interwoven with the spines in said proximal spine areas; and
 (d) a plurality of contiguous helical turns continuing from said proximal helical turns to the proximal end of said spines.

5. A laser-energizable thermal probe assembly according to claim 1 wherein said securing means comprises at least a portion of said helical turns around said proximal spine areas of said spines being crimped into said fiber jacket.

6. A laser-energizable thermal probe assembly according to claim 1, wherein said securing means includes a cured mass of a biocompatible adhesive extending from the contiguous helical turns over the neck portion to the proximal helical turns.

7. A laser-energizable thermal probe assembly according to claim 1 including a thermocouple secured proximate and in operative thermal relationship to said probe body to sense the surface temperature of said probe body, and a pair of thermocouple leads extending from said thermocouple.

8. A laser-energizable thermal probe assembly as claimed in claim 4 wherein said contiguous helical turns continuing from said proximal helical turns to the proximal end of said spines are crimped into said fiber jacket to provide said securing means.

9. A laser-energizable thermal probe assembly according to claim 8 in which said thermocouple leads are encased with insulating material and protrude externally from the jacket between adjacent helical turns with the ends of said thermocouple leads being attached to an exterior surface of the curvoidal tip.

10. A laser-energizable thermal probe assembly according to claim 9 wherein the series of helical turns comprises:
 (a) a plurality of contiguous helical turns extending from the probe body neck portion to the central spine areas;
 (b) at least one non-contiguous helical turn extending from the contiguous helical turns to the proximal spine areas;
 (c) a plurality of proximal helical turns interwoven with the spines in said proximal spine areas; and
 (d) a plurality of contiguous helical turns continuing tô the proximal end of said spines, said plurality of turns being crimped into the fiber jacket to provide at least a portion of said securing means.

11. A laser-energizable thermal probe assembly according to claim 10 wherein said securing means includes a cured mass of a biocompatible adhesive potted over and extending from the contiguous helical turns over the neck portion to the proximal helical turns.

12. A laser-energizable thermal probe assembly according to claim 10 wherein said wires are formed of a metal selected from the group consisting of platinum, iridium, stainless steel and alloys thereof.

* * * * *